(12) United States Patent
Southworth

(10) Patent No.: US 6,755,866 B2
(45) Date of Patent: Jun. 29, 2004

(54) PROSTHETIC STEM WITH BEARINGS

(75) Inventor: Carleton B. Southworth, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

(21) Appl. No.: 10/224,009

(22) Filed: Aug. 20, 2002

(65) Prior Publication Data

US 2004/0039451 A1 Feb. 26, 2004

(51) Int. Cl.⁷ .................................................. A61F 2/38
(52) U.S. Cl. ............................. 623/23.23; 623/23.25; 623/23.26; 623/23.12
(58) Field of Search ............................ 623/23.23, 23.25, 623/23.26, 23.17, 22.14, 22.15, 23.46

(56) References Cited

U.S. PATENT DOCUMENTS

| | | |
|---|---|---|
| 3,855,638 A | 12/1974 | Pilliar |
| 4,080,666 A | 3/1978 | Fixel |
| 4,302,855 A | 12/1981 | Swanson |
| 4,314,381 A | 2/1982 | Koeneman |
| 4,337,773 A | 7/1982 | Raftopoulos et al. |
| 4,344,190 A | 8/1982 | Lee et al. |
| 4,546,501 A | 10/1985 | Gustilo et al. |
| 4,589,883 A | 5/1986 | Kenna |
| 4,636,214 A | 1/1987 | Homsy |
| 4,697,584 A | 10/1987 | Haynes |
| 4,718,912 A | 1/1988 | Crowninshield |
| 4,738,681 A | 4/1988 | Koeneman et al. |
| 4,808,186 A | 2/1989 | Smith |
| 4,813,963 A | 3/1989 | Hori et al. |
| 4,851,008 A | 7/1989 | Johnson |
| 4,895,573 A | 1/1990 | Koeneman et al. |
| 4,911,720 A | 3/1990 | Collier |
| 4,986,834 A | 1/1991 | Smith et al. |
| 4,988,359 A * | 1/1991 | Frey et al. ................ 623/23.25 |
| 5,002,575 A | 3/1991 | Johnson |
| 5,007,931 A | 4/1991 | Smith |
| 5,035,717 A | 7/1991 | Brooks |
| 5,092,899 A | 3/1992 | Forte |
| 5,152,799 A | 10/1992 | Lyons |
| 5,193,679 A | 3/1993 | White |
| 5,197,989 A | 3/1993 | Sapozhnikov et al. |
| 5,219,363 A | 6/1993 | Crowninshield et al. |
| 5,222,985 A | 6/1993 | Homsy |
| 5,316,550 A | 5/1994 | Forte |
| 5,336,265 A | 8/1994 | Serbousek et al. |

(List continued on next page.)

FOREIGN PATENT DOCUMENTS

| | | |
|---|---|---|
| EP | 0 346 294 A1 | 5/1989 |
| EP | 0 700 670 A1 | 3/1995 |
| WO | 9407438 A | 4/1994 |
| WO | WO 99/15113 A1 | 4/1999 |
| WO | WO 01/60288 A1 | 8/2001 |

Primary Examiner—Pedro Philogene
Assistant Examiner—David A Bonderer

(57) ABSTRACT

A joint prosthesis (10) for cooperation with a long bone (12) and a second bone (26) for use in arthroplasty is provided. A cavity (20) is formed in the long bone (12) and defined by an inner wall (30) of the long bone (12). The prosthesis (10) includes a stem component (32) including a distal portion (34) of the stem component (32) for placement at least partially within the cavity (20) of the long bone (12) and for securing to the long bone (12). The stem component (32) defines a longitudinal axis (36) of the stem component (32). The prosthesis (10) also includes a second component (32) securable to the second bone (26) and for cooperation with the stem component (32). The prosthesis (10) further includes a bearing (40) for placement in the cavity (20) between the stem component (32) and the long bone (12) so that the distal portion of the stem component (32) is spaced from the inner wall (30) of the long bone (12).

17 Claims, 16 Drawing Sheets

U.S. PATENT DOCUMENTS

| | | |
|---|---|---|
| 5,405,005 A | 4/1995 | White |
| 5,405,394 A | 4/1995 | Davidson |
| 5,443,512 A | 8/1995 | Parr et al. |
| 5,507,830 A | 4/1996 | DeMane et al. |
| 5,702,483 A | 12/1997 | Kwong |
| 5,755,805 A | 5/1998 | Whiteside |
| 5,775,720 A | 7/1998 | Kmiec et al. |
| 5,861,042 A | 1/1999 | Buechel et al. |
| 5,897,560 A | 4/1999 | Johnson |
| 5,899,942 A | 5/1999 | Berman |
| 5,997,581 A | 12/1999 | Khalili |
| 6,110,179 A | 8/2000 | Flivik et al. |
| 6,123,730 A * | 9/2000 | Ling et al. ............... 623/23.25 |
| 6,126,691 A * | 10/2000 | Kasra et al. ............. 623/18.11 |
| 6,217,620 B1 * | 4/2001 | Park ....................... 623/23.26 |
| 6,228,123 B1 | 5/2001 | Dezzani |
| 2003/0074080 A1 * | 4/2003 | Murray ................... 623/22.42 |

* cited by examiner

PROSTHETIC STEM WITH BEARINGS

TECHNICAL FIELD OF THE INVENTION

The present invention relates generally to the field of orthopaedics, and more particularly, to an implant for use in arthroplasty.

BACKGROUND OF THE INVENTION

The invention relates to implantable articles and methods for manufacturing such articles. More particularly, the invention relates to bone prostheses and processes for manufacturing the same.

There are known to exist many designs for and methods for manufacturing implanted articles, such as bone prostheses. Such bone prostheses include components of artificial joints, such as elbows, hips, knees, and shoulders. An important consideration in the design and manufacture of virtually any implantable bone prosthesis is that the prosthesis has adequate fixation when implanted within the body.

Early designs of implantable articles relied on the use of cements, such as polymethylmethacrylate to anchor the implant. The use of such cements can have some advantages, such as providing a fixation that does not develop free play or does not lead to the erosion of the joining bone faces post-operatively. However, the current trend is to use the cements to a lesser extent because of their tendency to lose adhesive properties over time and the possibility that the cement contributes to wear debris within a joint. Implantable articles, which are not implanted with the use of cements, are implanted by providing a cavity for the implant that matches the geometry of the implant and then press fitting the implantable article into the cavity.

Whether utilizing cement or the press-fitting technique for the implantable articles, a problem has been observed which relates to the proper distribution of stresses within the prosthesis and throughout the surrounding bone. This problem can best be described with references to Wolff's Law. This Law is generally based on the human anatomy of principles of atrophy. According to the principle of atrophy, when a human tissue is under utilized, it will atrophy or deteriorate. Conversely, as human tissue is utilized, it will grow and strengthen. According to Wolff's Law, this phenomenon can describe the conditions on human bone, particularly when that bone is used in conjunction with an implantable prosthesis.

According to Wolff's Law, atrophy is defined as the thinning of the cortex with retention of normal cortical texture. According to Wolff's Law, hypertrophy will occur at the area of highest stress surrounding an implant. The thickening of the cortex is a very desirable event in the post-operative patient. For many implants within a long bone, the location of hypertrophy is often at that distal end of the implant. This is caused by the artificially raised stresses at the point of sudden transition from the flexible distal femur to the artificially stiffened proximal femur. This is true both for press fit and cemented stems. This phenomenon of hypertrophy does result in excellent adhesion in the diaphysis but results in a less than desirable condition between the implant and the long bone in the metaphesis.

If too little stress is applied to the bone, resorption can occur leading to atrophy of the affected area. Too much stress may also lead to resorption in atrophy, or may result in an undesirable atrophy of the affected area. Accordingly, there exists a need for an improved joint prosthesis, that addresses the needs and problems of prior joint designs as it relates to the distribution of stress.

The phenomenon of atrophy resulting from insufficient loading at certain portions of the implant and bone interface has been referred to as stress shielding.

Stress shielding has been addressed by putting a porous coating only on the proximal portion of the joint prosthesis and using a highly refined surface on the distal surface of the prosthesis. The porous coating is utilized to encourage the growth of hard tissue around the implant. The bone attachment usually occurs and growth is promoted when the surface of the implantable bone prosthesis is regular or textured. The interactions of newly formed hard tissue in or around the texture surface of the implantable bone prosthesis has been found to provide a good fixation for the prosthesis within the bone.

The designs where the porous coating is placed only on the proximal portion of the bone of the joint prosthesis attempt to duplicate the natural transmission of the load in the long bone. Such design may be associated with leg pain.

Attempts to reduce stress shielding include various attempts to make the stem more flexible. These efforts have included the clothespin design or central opening in the prosthesis. Another attempt is the use of altering the cross section of the stem of the prosthesis along its length. Another method of making the stem more flexible is the use of alternate materials.

These efforts, which are aimed at making the stem more flexible, are expensive and in each case allow the distal portion of the prosthesis to rub against the inside of the bone canal as the bone flexes. This may be painful to the patient and may induce a natural bone growth near the distal end of the prosthesis as the prosthesis rubs against the inside of the bone canal.

These attempts at making the stem more flexible by making the stem smaller or of a material with less strength may increase the probability that the stem will fracture in the long bone. Further, the use of the more flexible material may require that their size be larger and they may require that a larger amount of bone must be reamed from the bone canal.

The natural anatomy of the long bone is arcuate and curved in the central portion of the long bone. For use in revision surgery and when a fracture has occurred in the long bone, prostheses have been developed which are fitted into the more distal curved portion of the long bone. Such stems have been designed with curved distal portions. It can be difficult to prepare the long bone canal to accept a curved stem and accurate insertion can therefore be challenging. Devices with these features are expensive to produce and a large number of sizes and shapes are required to fit the individual anatomy including the need to obtain the proper ante-version in the patient.

Efforts have been made to reduce the instance of point stress associated with the distal portion of the prosthesis stems. As mentioned earlier, the point stress may lead to leg pain and also such high point stress is located at the distal portion of the prosthesis stem. The distal point stress may lead to fracture resulting from trauma or sub optimal bone quality. Bullet-shaped tips have met with some success but still cause some stress concentration at the distal portion of the implant.

While attempts have been made to improve the physiological loading of the bone to reduce stress shielding, the prior art efforts have met with limited success.

Accordingly, a new prosthesis is needed which improves the physiological loading of the bone and thereby reduces stress shielding type pain, as well as the probability of a stem fracture of the long bone.

SUMMARY OF THE INVENTION

The present invention is an element in the form of a linear bearing that is placed in the canal of the long bone. It is designed to mate with the stem of a prosthetic joint or an intermedullary rod. Typically, stems or rods used with this device would be smaller in diameter than existing orthopedic implants and would not contact the interior cortex of a long bone. Instead, the present invention would allow the stem or rod to guide or slide up and down in a central bushing.

One or more of the linear bearings may be used in conjunction with a single stem or intermedullary rod. The device allows a long bone, for example, a femur, to bend under load without shielding the bone from the normal stress patterns nearly as much as conventional designs of orthopedic joint implants do. The present invention places compressive forces almost exclusively in the proximal portion of the prosthetic joint. The linear bearing may include an articulating feature within the canal of the long bone.

The outer surface of the linear bearing of the present invention may be porous coated. The porous coating is designed to promote bone in-growth. The inner diameter of the linear bearing of the present invention is a bearing surface that captures the stem of a prosthetic joint member and holds it in axial alignment, but allows the stem to move up and down as psychological loads are applied to the long bone causing the long bone to bend. Accordingly, the stem of the prosthesis does not fill the bone canal and the stem may be made more flexible than current stem designs.

The linear bearing of the present invention does not require the canal of the long bone to be reamed down to the cortical bone over the length of the stem. Instead, an area in the bone canal may be prepared to receive the linear bearing with a hone that may be inserted into the canal at a depth where the linear bearing is to be placed. Centrifugal force may then be used to expand the hone as power is applied. The hone could be designed with shoes to prevent too much penetration of cortical bone. Alternately, a boring bar could be used for the same purpose. The boring bar can be inserted into a bore to make a larger diameter bore down lower.

The linear bearing of the present invention may be in the form of a simple -C- that is designed to be hammered down into position (or compressed and released into position) with the inner surface somewhat convex to accommodate the small deviation in placement where the center line of the linear bearing is not exactly parallel to the axis of the long bone canal.

According to one embodiment of the present invention, a joint prosthesis for cooperation with a long bone and a second bone for use in arthroplasty is provided. A cavity is formed in the long bone and is defined by an inner wall of the long bone. The prosthesis includes a stem component including a distal portion of the stem component for placement at least partially within the cavity of the long bone and for securing it to the long bone. The stem defines a longitudinal axis of the stem. The prosthesis also includes a second component securable to the second bone and for cooperation with the stem component. The prosthesis further includes a bearing for placement in the cavity between the stem and the long bone so that the distal portion of the stem component is spaced from the inner wall of the long bone.

According to another embodiment of the present invention, a hip joint prosthesis for cooperation with a femur and an acetabulum for use in arthroplasty is provided. A cavity is formed in the femur and is defined by an inner wall of the femur. The prosthesis includes a femoral component having a portion of the femoral component for placement at least partially within the cavity of the femur. The femoral component defines a longitudinal axis of the femoral component. The prosthesis also includes a cup for attachment to the acetabulum and for cooperation with said femoral component. The prosthesis further includes a bearing for placement in the cavity between the femoral component and the femur so that the distal portion of the femoral component is spaced from the inner wall of the femur.

According to yet another embodiment of the present inventions stem component for use in a joint prosthesis for cooperation with a long bone for use in arthroplasty is provided. A cavity is formed in the long bone. The stem component has portions of the stem component for placement at least partially within the cavity of the stem component. The stem component defines a longitudinal axis of the stem component. The distal portion of the stem component is spaced from the long bone.

According to another embodiment of the present invention, a bearing for use in a joint prosthesis for use in arthroplasty is provided. The bearing is adapted for cooperation with a stem component placed at least partially in a cavity formed in a long bone and defined by an inner wall of the long bone. The bearing is adapted for placement in the cavity between the stem component and the long bone so that the distal portion of the stem component is spaced from the inner wall of the long bone.

According to a further embodiment of the present invention, a method for performing joint arthroplasty including the steps of preparing a cavity in the medullary canal of a long bone, providing a bearing for implantation within the cavity, installing the bearing in the cavity, providing a stem for implantation at least partially within the cavity, and installing the stem to the bearing so that the distal portion of the stem is spaced from the long bone is provided.

The technical advantages of the present invention include the physiological loading of the bone in order that stress shielding may be reduced which may lead to retention of natural bone and the potential increase in thickness of cortical bone.

For example, according to one aspect of the present invention, a stem or rod is utilized with a linear bearing that is positioned within the medullary canal of a long bone such that the stem or rod may slide up and down in a central bushing. The device allows a long bone to bend under load without shielding the bone from normal stress patterns such as that of a press fitted conventional stem.

Thus, the present invention provides for a prosthetic joint component, which improves the physiological loading of the bone, thus reducing stress shielding.

Another technical advantage of the present invention is the reduced leg pain. For example, according to one aspect of the present invention, the stem or rod used in conjunction with the linear bearing of the present invention is smaller in diameter than the medullary canal, and thus, the stem or rod is not in contact at its distal point with the bone. Without the linear bearing the contact of the stem to the bone distally may cause a portion of a prosthesis stem to rub against the inside of a bone canal as the bone flexes, causing pain. Thus, the present invention provides for reduced leg pain caused by the rubbing of a stem against the inside of the bone canal.

Another technical advantage of the present invention is the reduced probability that a stem will fracture in the long bone as a result of trauma. For example, accordingly to one aspect of the present invention, the stem or rod used in conjunction with the linear bearing of the present invention is smaller in diameter distally than the canal of the long bone. The use of a stem or rod smaller than the canal reduces the force transmitted to the long bone as a result of trauma and thus reduces the probability that a stem will fracture as a result of trauma. Thus, the present invention provides for a reduction in the probability that a stem will fracture the long bone as a result of trauma.

Additionally, the present invention reduces the amount of bone that must be reamed from the bone canal. For example, according to one aspect of the present invention, a hone can be inserted into the canal at a depth where the linear bearings are to be placed and only that portion of the long bone needs to have bone removed so that the linear bearings may be placed at that location. Thus, the present invention reduces the amount of bone that must be removed from the bone canal.

In addition, the present invention includes the technical advantage of allowing straight stems smaller than the canal diameter to be inserted past curved portions of the long bone and still remain effective. For example, according to one aspect of the present invention, the stems or rods used with the linear bearing are smaller in diameter than current designs and are allowed to be smaller than the bone canal. Thus, straight stems may be inserted past curved portions of the long bone.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
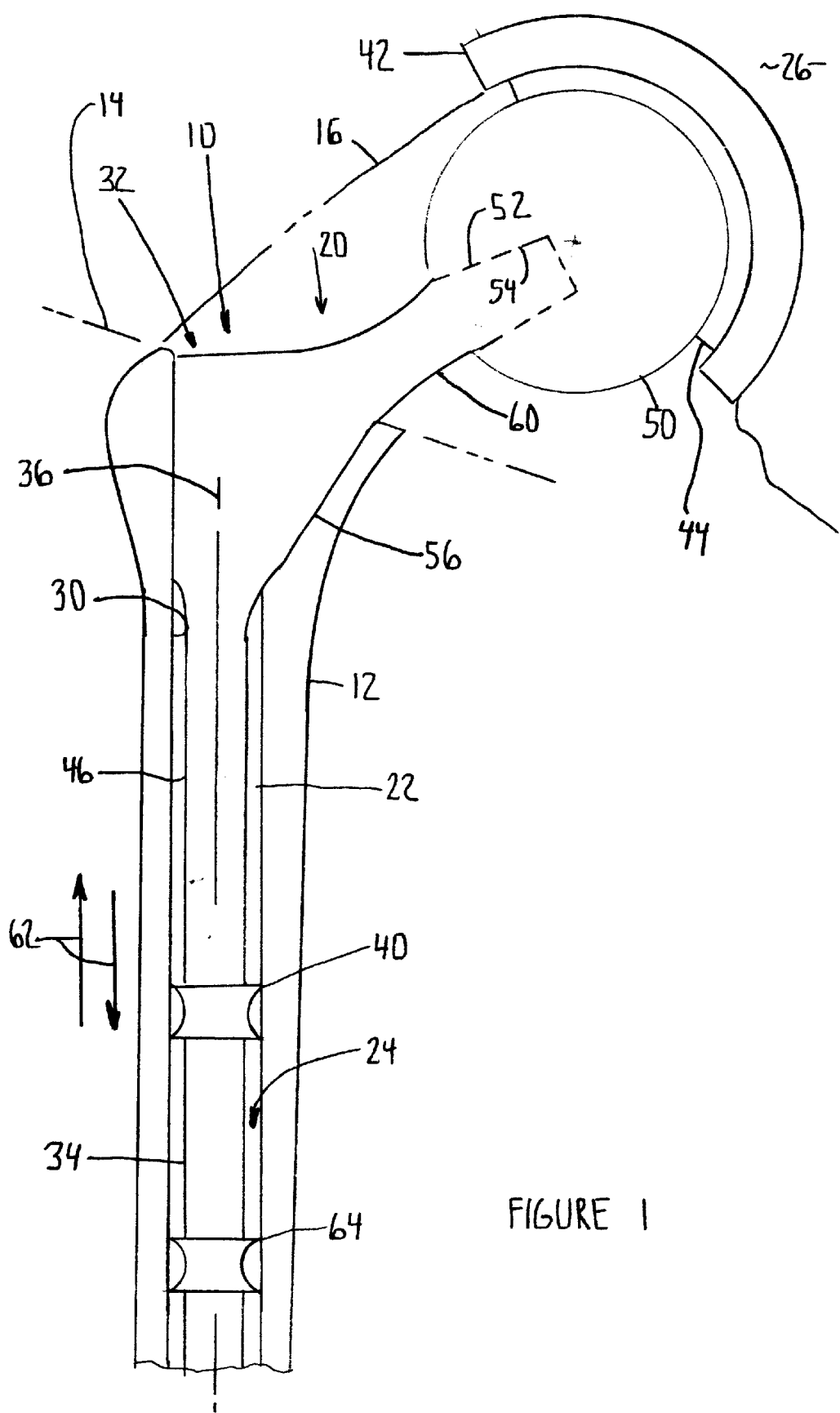
FIG. 1 is a plan view partially in cross section of a hip prosthesis including a stem, bearings, ball and cup implanted into a femur and acetabulum in accordance with an embodiment of the present invention.

According to the present invention and referring now to FIG. 1, joint prosthesis 10 is shown for use in arthroplasty. Arthroplasty is a well-known procedure for the treatment of osteoarthritis. A further explanation of arthroplasty may be found in Charnley, Sir John. Low Friction Arthroplasty of the Hip. New York: Springer, Verlock, Berlin, and Heidelberg, 1979 incorporated herein by reference in its entirety.

The joint prosthesis 10 is positioned in a long bone 12. While the long bone 12 may be any long bone within the human anatomy, the present invention is particularly well suited for long bones, which have an arcuate shape or are subject to large loads. For example, the long bone 12 may be in the form of a humerus or, as shown in FIG. 1, a femur.

The femur 12 is resected along resection line 14 relieving the epiphysis 16 from the femur 12. The prosthesis 10 is implanted in the femur 12 by positioning the prosthesis 10 in a cavity 20 formed in a portion of cancellous bone 22 within medullary canal 24 of the femur 12.

The joint prosthesis 10 is utilized for articulating support between a long bone, for example femur 12, and a second bone, -for example, acetabulum 26. The cavity 20 in the long bone 12 is defined by an inner wall 30 of the long bone 12.

The joint prosthesis 10 includes a stem component 32. The stem component 32 includes a distal portion 34, which is placed at least partially within the cavity 20 of the long bone 12. The stem component 32 defines a longitudinal axis 36 of the stem component 32.

The prosthesis 10 further includes a bearing 40 for placement in the cavity 20 of the long bone 12 between the stem component 32 and the long bone 12. The bearing 40 is utilized to secure the stem component 32 to the long bone 12. The bearing 40 is utilized to space the stem component 32 from inner wall 30 of the long bone 12.

As shown in FIG. 1, the joint prosthesis 10 may further include a cup 42, which is connected to the natural acetabulum 26. The stem 32 is operably connected to the cup 42. The stem 32 may be in direct contact with the cup 42 or may, as shown in FIG. 1, include a liner 44 positioned between the cup 42 and the stem 32. The cup 42 may be made of a suitable, durable material, which is compatible with the human anatomy. For strength and durability, typically, the cup 42 is made of a metal such as stainless steel, cobalt chrome alloy, or titanium or may be made of a ceramic material.

The liner 44 may be made of any suitable bearing material and is often made of a polyethylene, for example, ultra high molecular weight polyethylene (UHMWE). Alternately, the liner 44 may be made of a ceramic material.

While stem component 32 may be made of a unitary construction, typically, the stem component 32 includes a stem portion 46 and a head portion 50. The two-part construction of the stem component 32 provides for easier manufacture of and for varying offsets for the prosthesis by utilizing a plurality of head portions 50 and or a plurality of stem portions 46.

The stem portion 46 may be connected to the head portion 50 in any suitable fashion. For example, the stem portion 46 may include a male taper portion, 52 which mates with a female taper portion 54 on the head portion 50.

As shown in FIG. 1, the stem portion 46 may include a body or proximal stem portion 56. The distal stem portion 34 extends downwardly from the proximal stem portion 56 and a neck portion 60 extends upwardly from the proximal stem portion 56. The proximal stem portion 56 and the distal stem portion 34 are preferably located within the cavity 20 formed within the cancelous bone 22 of the medullary canal 24.

Preferably, as shown in FIG. 1, the linear bearing 40 serves to permit the stem component 32 to be designed such that body or proximal portion 56 of the stem component 32 is in intimate contact with the inner wall 30 of the long bone or femur 12. The contact and support of the stem component 32 of the joint prosthesis 10 by the body 56 provides for proximal loading of the long bone 12. The proximal loading provides optimum support of the prosthesis and leads to growth and formation of cortical bone around the proximal long bone.

The bearing 40 may be situated in the canal 24 so that the distal portion 34 of the stem component 32 may be freed to move in the direction of arrows 62 so that no vertical support is lent by the bearing 40 to the joint prosthesis 10. The absence of axial support by the bearing 40 may be accomplished by permitting the bearing to move relative to the bone or the bearing to move relative to the distal portion 34 of the stem component 32. Preferably, as is shown in FIGS. 1–4, the bearing 40 is fixedly secured to the long bone 12 and the distal portion 34 of the stem component 32 is permitted to move axially relative to the bearing 40.

While the invention as shown in FIG. 1 may be practiced with a solitary bearing 40, it should be appreciated that additional bearings, for example, second bearing 64, may be positioned in a spaced-apart relationship from the bearing 40. The second bearing 64 may have a similar shape, size, and configuration as the bearing 40.

Figure 2:
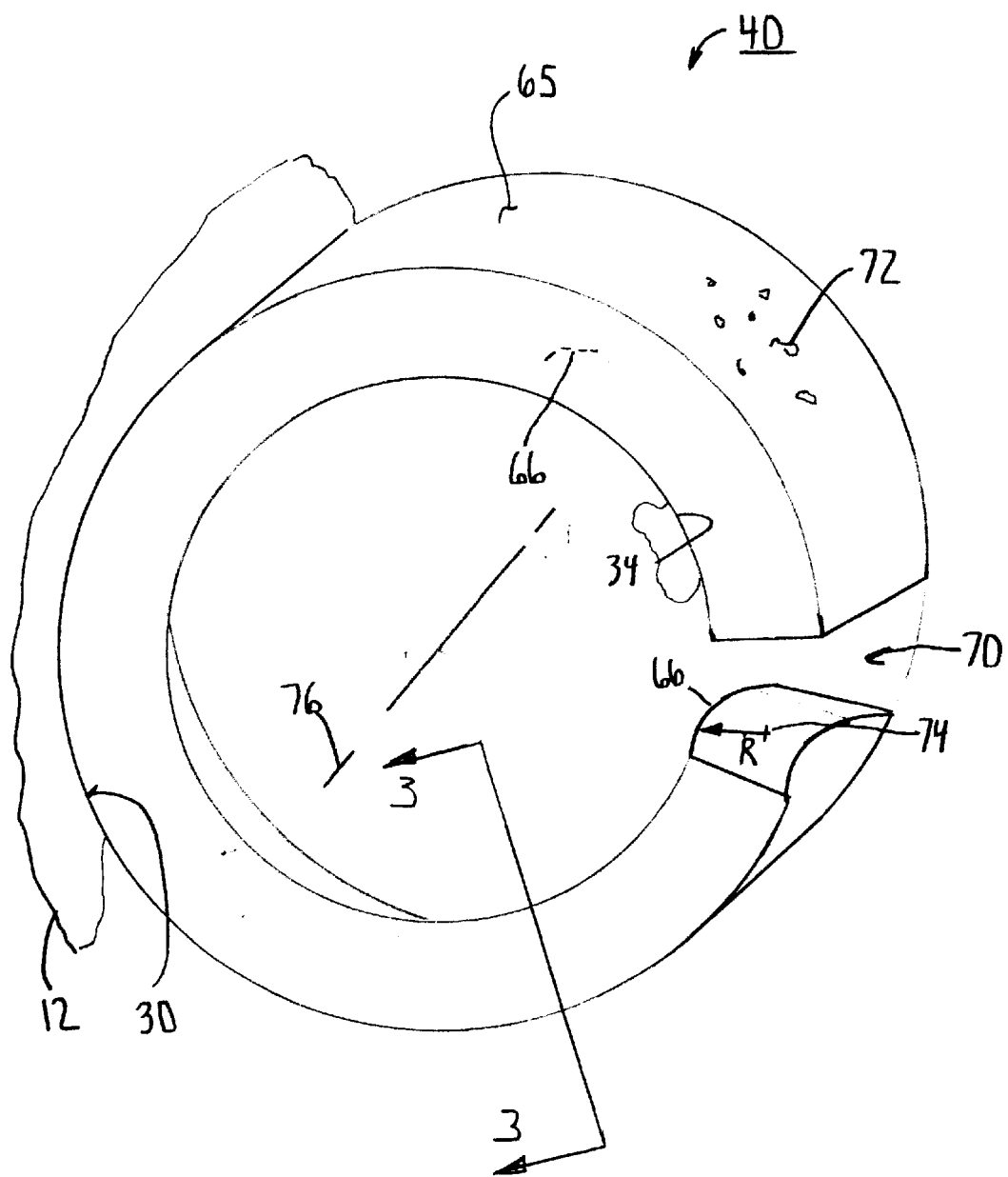
FIG. 2 is a perspective view of the bearing of the present invention for use with the hip prosthesis of FIG. 1.
Figure 3:
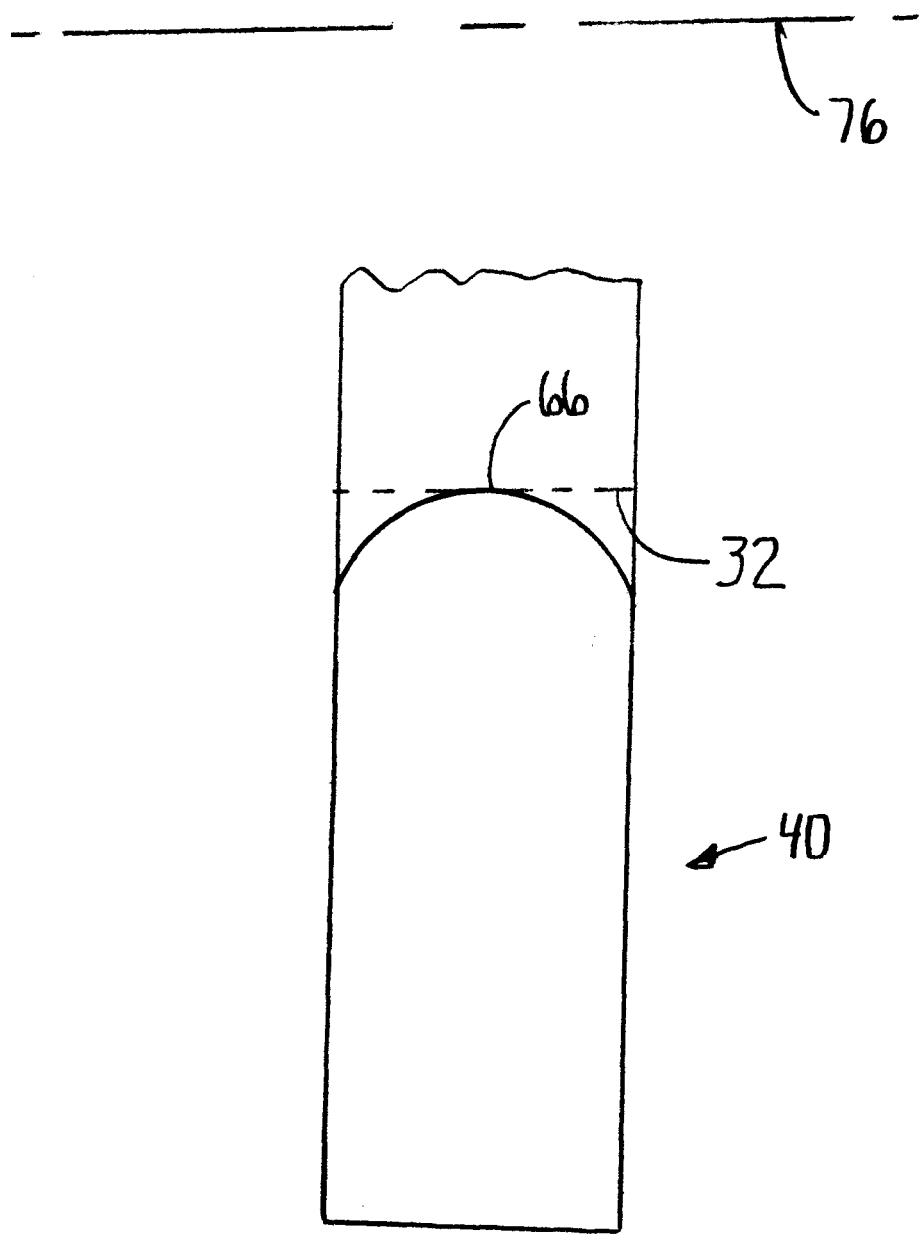
FIG. 3 is a cross-sectional view of the bearing of FIG. 2 along the line 3—3 in the direction of the arrows.

Referring now to FIGS. 2 and 3, the bearing 40 is shown in greater detail. The bearing 40 includes an outer surface 65 for contact with the inner wall 30 of the long bone 12 and an inner surface 66 for contact with distal portion 34 of the stem component 32. The bearing 40 may be in the form of a ring defined by outer surface 65 and inner surface 66. Alternatively, as shown in FIGS. 2 and 3, the bearing 40 may be in the form of a split ring including a transverse opening 70 to permit the bearing 70 to be collapsed to insert the bearing 40 into the cavity 20 (see FIG. 1).

The outer surface 65 may have any suitable shape to mate with the inner wall 30 of the long bone 12 and for simplicity may have a circular outer periphery. The outer surface 65 may include a feature 72 for promoting bone ingrowth between the bearing 40 and the long bone 12. For example, the feature 72 may be in the form of a porous coating, for example, Porocoat®, a coating sold by the Assignee of the instant application. The coating is more fully described in U.S. Pat. No. 3,855,638 to Pilliar and hereby incorporated by reference in its entirety.

The inner surface 66 of the bearing 40 may have any suitable shape capable for contact with the distal portion 34 of the joint prosthesis 10. For example, the inner surface 66 maybe have a generally cyclical shape. Further as mentioned before, the inner surface 66 may be adapted for relative motion between the bearing 40 and the distal portion 34 of the stem. The inner surface 66 of the bearing 40 may be in clearance with the distal portion 34 to permit movement in the direction of arrows 62 (see FIG. 1).

Preferably, as shown in FIG. 2 and 3, the inner surface 66 has a shape adapted to permit angular movement of the stem component 32 of the joint prosthesis 10 with respect to the long bone 12 along the longitudinal axis 36 of the stem component 32. The angular motion may be permitted by sufficient clearance between the bearing 40 and the stem component 32, by providing for a multi-piece bearing with portions which move relative to other portions of the bearing 40 or by the use of a contour inner surface 66 as shown in FIGS. 2 and 3. The bearing 40 as shown in FIGS. 2 and 3, may have a convex inner surface 66. The inner surface 66 may be defined by a radius R extending from centerline 74 that is centrally located along longitudinal axis 76 of the bearing 40. The convex shape of the periphery inner surface 66 permits the bearing 40 to pivot about longitudinal axis 76 of the bearing 40 and consequently to pivot about the longitudinal axis 36 of the stem component 32.

Referring now to FIG. 3, the inner surface 66 of the bearing 40 is shown in greater detail. The inner surface 66 permits the stem component 32 to pivot about longitudinal axis 76 of the bearing 40.

Figure 4:
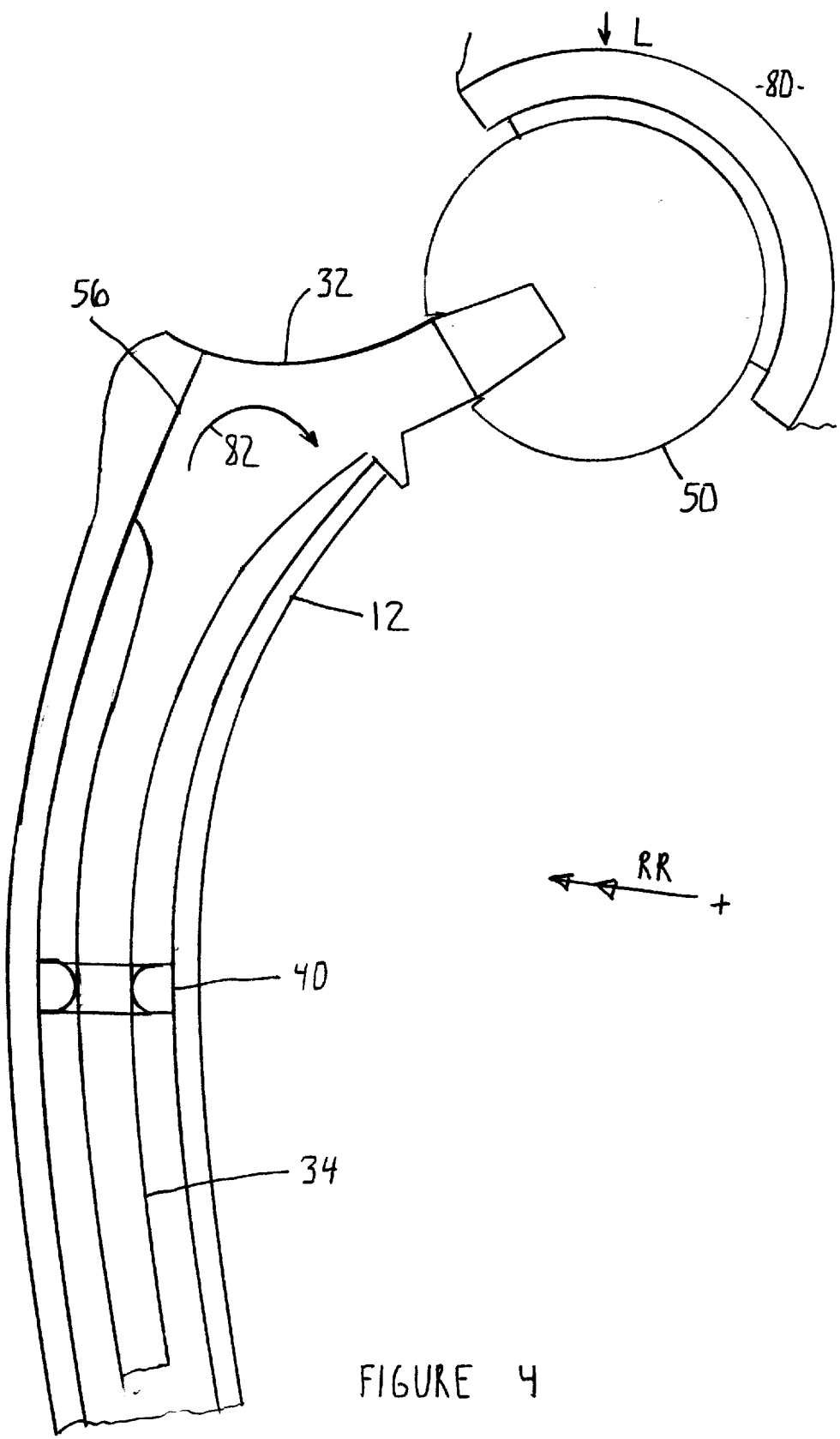
FIG. 4 is a plan view partially in cross section of the hip prosthesis of FIG. 1 showing the prosthesis being bent under load.

Referring now to FIG. 4, the joint prosthesis 10 is shown in position in the femur 12 when the femur 12 is under a load L. The load L from torso 80 causes the body 56 of the stem component 32 to rotate in the direction of arrow 82 such that the distal portion 34 of the stem component 32 and the femur 12 had an arcuate shape defined by radius RR. The bearing 40 serves to provide support for the stem component 32 without providing a bending torque on the stem component 32.

Typically, the hip prosthesis is secured to the medullary canal of the femur typically either by a press fit with a medullary canal or with the use of a cement mantle which is positioned between the prosthesis and cancellous bone.

In utilizing a cement mantle, the cavity is broached or reamed slightly larger than the stem and a quantity of cement (for example, PMMA (polymethylmethacrylate) is placed within the cavity and the stem inserted therein. A small uniform layer of, for example, one to four millimeters of cement, is formed between the stem component 32 and the in femur 12.

The bearing 40 may likewise be secured to the femur 12 by either a press fit with the femur 12 or through the use of PMMA. The outer surface 64 (see FIG. 2) of the bearing 40 is sized to either be smaller than the cavity 20 such that the PMMA may be used to secure the bearing 40 to the cavity 20, or the bearing 40 may be press fit into the canal.

Figure 5:
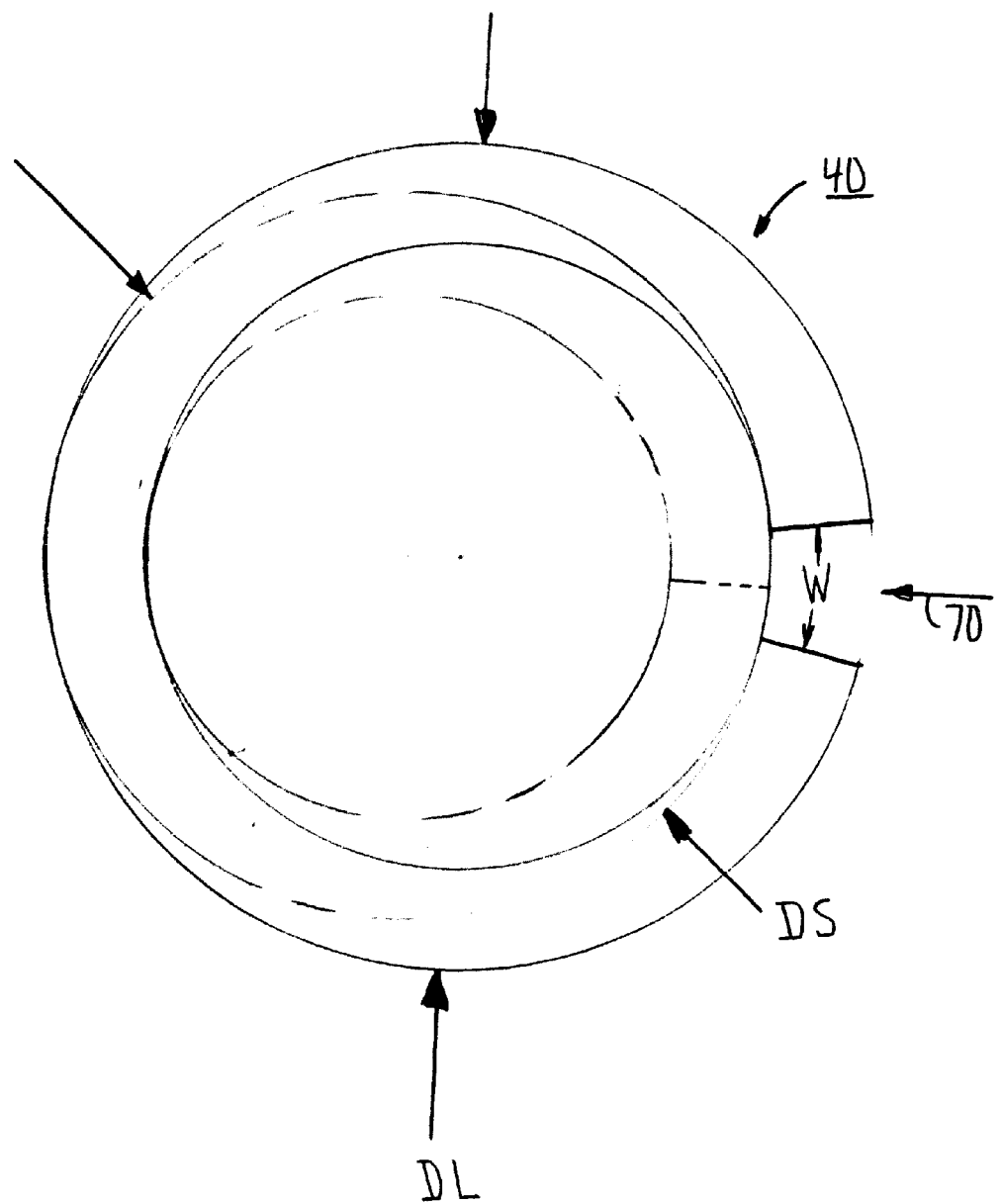
FIG. 5 is a plan view of the bearing of FIG. 2 showing the bearing in a compressed position in phantom for installation in the femoral canal.

Referring now to FIG. 5, since the bearing 40 includes the transverse opening 70 in the bearing, the bearing 40 may be compressed from a relaxed diameter DL to a compressed diameter DS which is smaller than the relaxed diameter DL. The resiliency of the material for which the bearing 40 is made can be utilized to provide the press fit or the interference of the bearing 40 with respect to the cavity 20. An instrument (not shown) maybe utilized to compress the bearing 40 to have it fit into the cavity 20.

Referring again to FIG. 1, it should be appreciated that any suitable combination of drilling, reaming, or broaching, can be used to form a cavity for receiving the prosthesis 10. Typically, a broach (not shown) is driven into the medullary canal 24 so that the prosthesis may be fitted into the cavity 20. The use of a reamer or broach is typically required in most prostheses in that the entire distal length of the joint prosthesis is intended to support the long bone 12. In contrast, the joint prosthesis 10 of the present invention utilizes the bearing 40 to provide a very limited contact between the prosthesis 10 and the long bone 12. Thus, utilizing the joint prosthesis 10 of the present invention permits the preparation of a limited contact area of the bearing 40 against the long bone 12.

According to the present invention, thus, the joint prosthesis 10 may be installed by preparing only a limited contact portion of the cavity 20. It is generally believe to be good practice to minimize the amount of bone removal necessary to install a prosthesis. Thus, where limited contact occurs, a limited preparation of the area around that contact is preferred.

Preparation of the bone canal around the bearing can be provided in a number of ways. Tools may be provided which provide for an anular groove in the bone cavity 20. Such tools include a boring bar, a rat tail file, a half-round file, a ball-end file, and a hone. Such hones include a stone/shoe hone as described below and a ball hone.

It should be appreciated that the bearing 40 may include a cutting edge (not shown)extending from outer surface 65 of the bearing to prepare the bone canal. Alternatively, the outer surface 65 of the bearing 40 may be coated with an abrasive surface (not shown) to prepare the bone canal. The abrasive surface may be a porous coating. The bearing 40 may be mounted onto a tool (not shown) to assist in utilizing the bearing 40 to prepare the bone canal. The tool may be rotated within and translated along the bone canal. The tool may be used to expand the outer surface of the bearing to engage the cutting edge or abrasive surfaces with the bone and may be used to contract the bearing for removal for cleaning the canal prior to bearing insertion.

Figure 6:
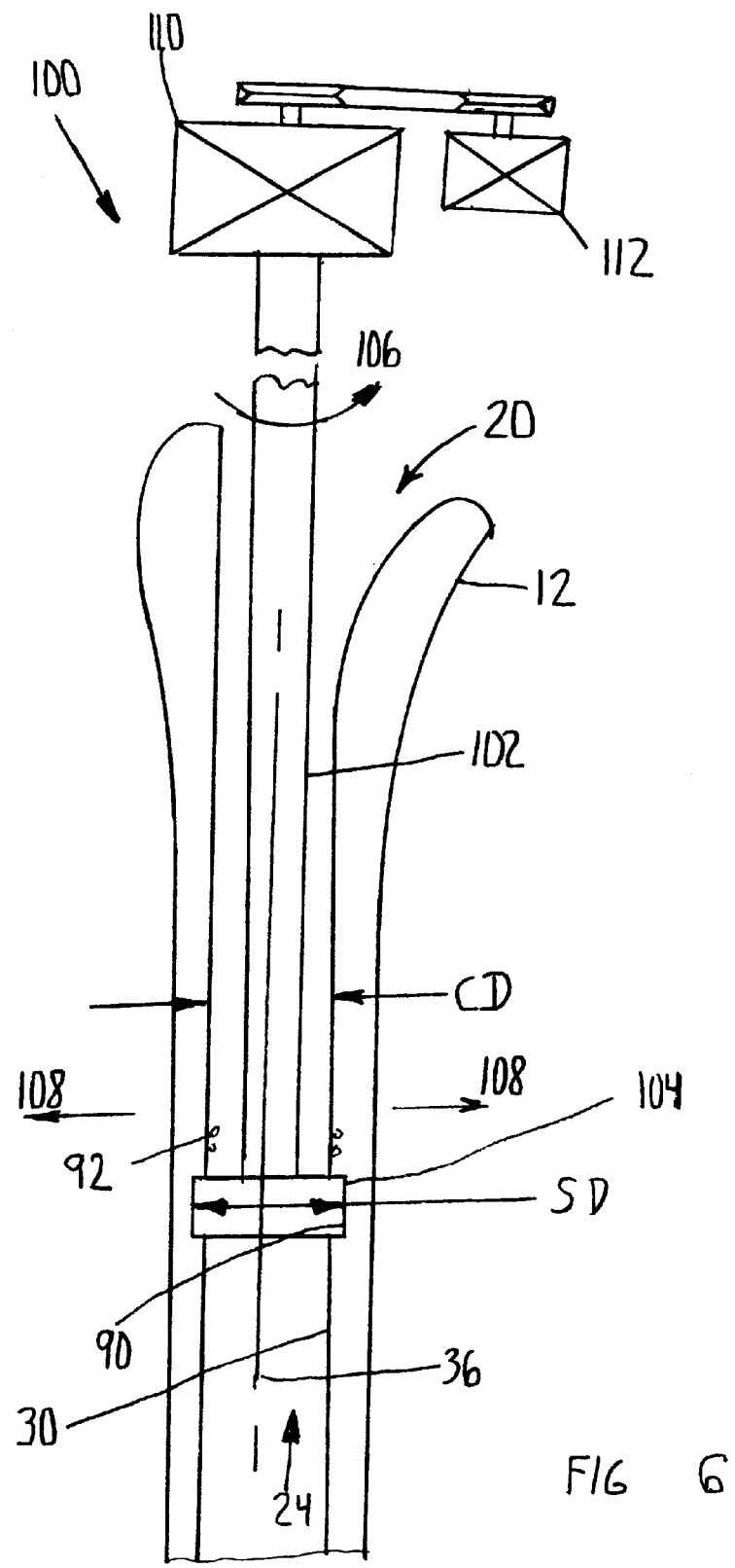
FIG. 6 is a plan view partially in cross section of a honing apparatus for preparing the femur in position with the hip prosthesis of FIG. 1.
Figure 7:
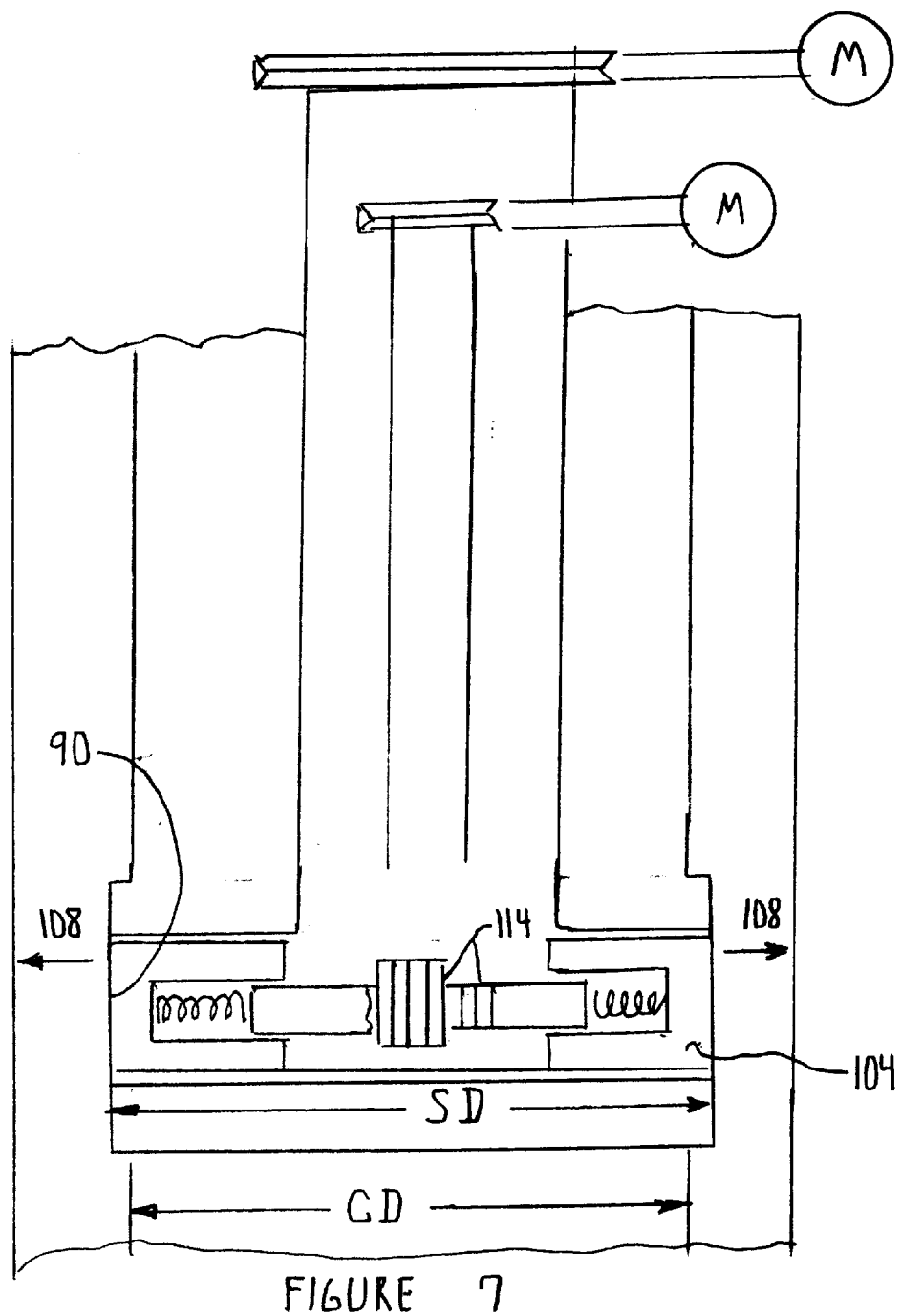
FIG. 7 is a partial plan view partially in cross section of the honing apparatus of FIG. 6.

Referring now to FIGS. 6 and 7, a hone is shown to prepare the contact area for the bearings according to the present invention.

Referring now to FIG. 6, a honing device 100 is shown in position in the femur 12. The honing device 100 is utilized to form a bearing seat 90 in the inner wall 30 of the femur 12 to provide a location for installing bearings 40 (see FIG. 1). The honing device 100 includes a shaft 102 for supporting the honing tool 104. The honing tool 104 may be in the form of sand paper or an abrasive stone. The honing device 100 typically rotates in the direction of arrow 106 to remove bone 92 from the femur 12 to form the bearing seat 90.

The honing device 100 is utilized because of its ability to remove only a minimal amount of cortical bone 90 to provide a bearing seat, which has a generally cylindrical shape. Only that amount of cortical bone 92, which is required to form a cylindrical seat 90, should be removed. The honing device 100 may rigidly rotate about the longitudinal axis 36 of the femur 12 or may permit the tool 104 to move outwardly in the direction of arrows 108 to assist in the removal of cortical bone 92. The honing device 100 may include a body 110, which supports the shaft 102. The honing device 100 may be powered by any suitable power source for example by motor 112.

Referring now to FIG. 7, the honing 100 is shown in greater detail. The honing device 100 may include gears 114 to advance the tool 104 outwardly in the direction of 108. As shown in FIG.7, the tool 104 is utilized to form the bearing seat 90 having a seat diameter SD.

Referring now to FIGS. 5, 6, & 7, the bearing 40 maybe compressed to diameter DS such that DS is smaller than diameter CD of the cavity 20 such that the bearing 40 maybe inserted into the canal 24 of the femur 12. When the bearing 40 is positioned at the bearing seat 90, the bearing 40 maybe released to permit the bearing 40 to reach its relaxed state having a diameter of DL. The diameter DL is preferably greater than the diameter SD of the bearing seat 90 formed by the honing device 100. Thus, the bearing seat may be formed for the bearing with a minimal amount of cancellus bone removal.

Figure 8:
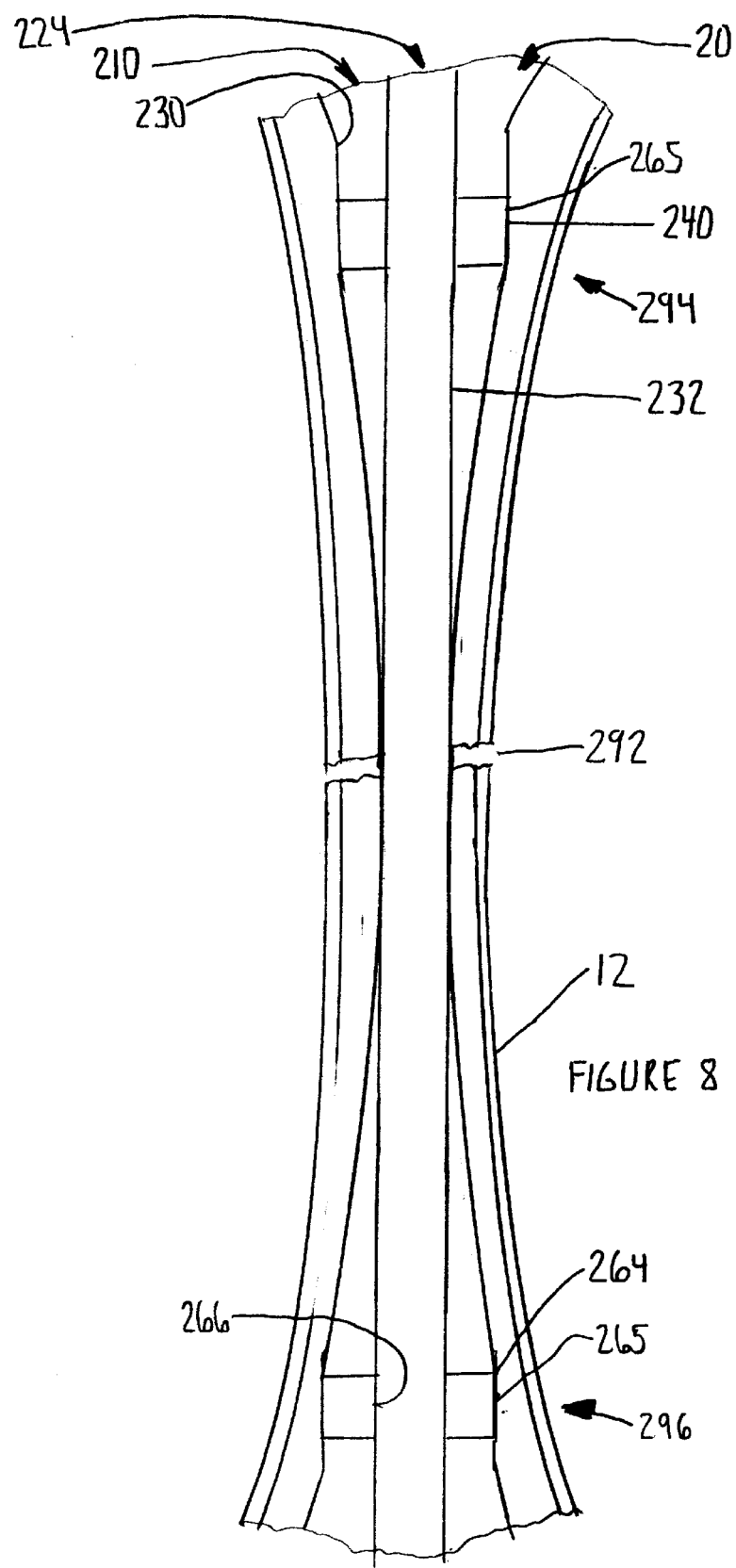
FIG. 8 is a plan view partially in cross section of an intermedullary nail implanted into a femur in accordance with a further embodiment of the present invention.

Referring now to FIG. 8, an alternate embodiment of the present invention is shown as a prosthesis in the form of intramedullary nail assembly 210. The nail assembly 210 is utilized to repair a fracture 292 in a long bone or femur 12. A first bearing 240 is positioned in a first portion 294 of the long bone 212 and a second bearing 264 is positioned in a second portion 296 of the long bone 12.

The bearings 240 and 264 are similar to the bearings 40 and 64 of FIGS. 1 through 4 and include an outer periphery 265 which is in contact with inner wall 230 of the femur or long bone 12 and an inner diameter 266 which slideably fits with the outer periphery of the intramedullary rod 232. Similarly to the joint prosthesis 10 of FIGS. 1 through 4, the inner wall 230 of the long bone 12 may be prepared for the bearing 40 at the location of contact of the bearings 40 by suitable tool, for example a hone.

As can be seen in FIG. 8, the IM rod 232 fills the canal 224 of the long bone 12 only at that place adjacent the fracture 292. In areas spaced from the fracture 292, the intramedullary rod 232 is spaced from inner wall. 230 of the long bone 12. The spacing between the rod 232 and the long bone 12 causes the transmission of stress in the healed bone to duplicate natural bone stress transmission more naturally.

Figure 9:
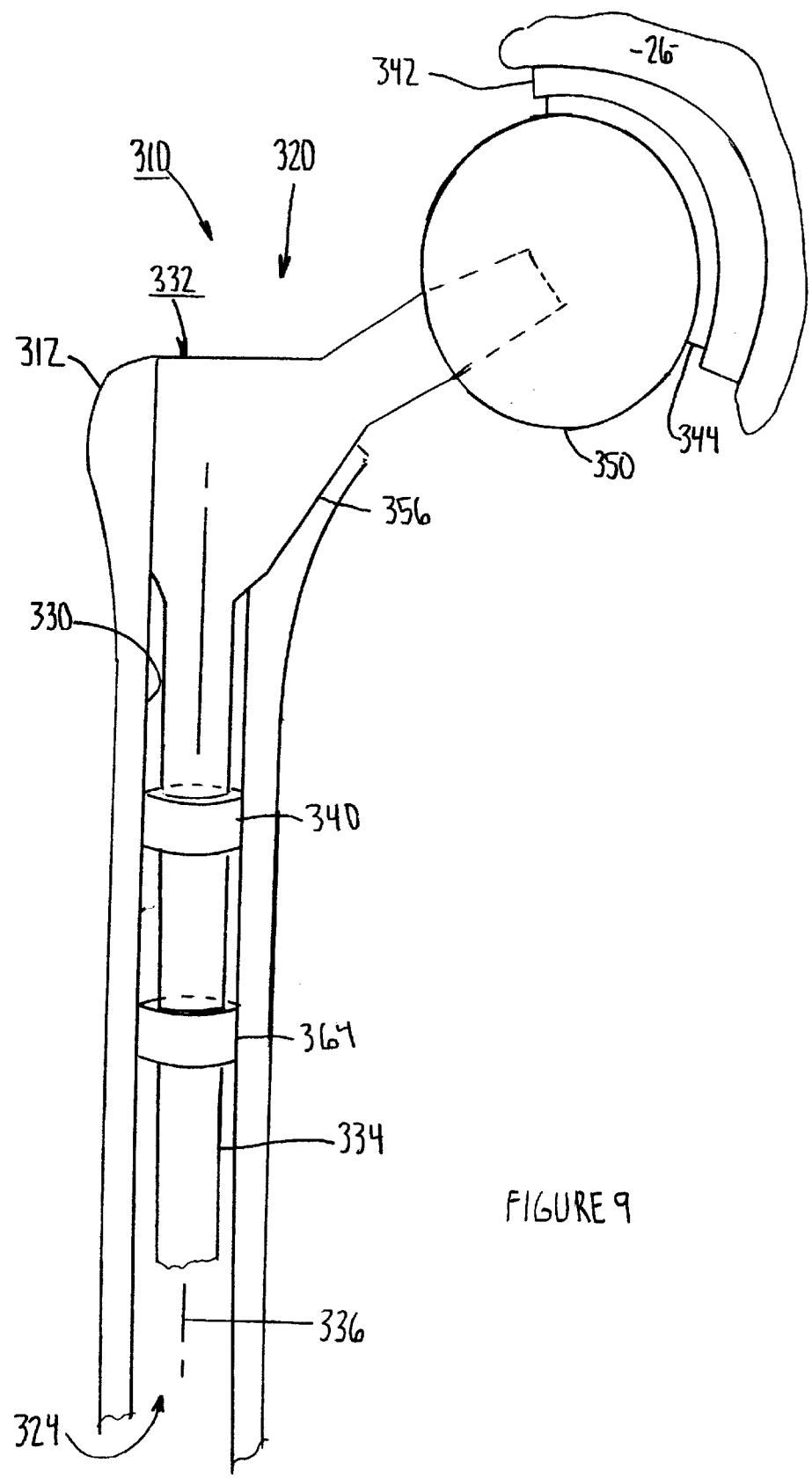
FIG. 9 is a partial perspective view partially in cross section of a hip prosthesis including a stem, bearings, ball and cup for implanting into a femur and acetabulum in accordance with another embodiment of the present invention.

Referring now to FIG. 9, an alternate embodiment of the present invention is shown as joint prosthesis 310. The joint prosthesis 310 is similar to joint prosthesis 10 of FIGS. 1 through 4, and includes a stem component 332 which is similar to stem component 32 of the joint prosthesis 10 of FIGS. 1 through 4. The joint prosthesis 310 also includes a bearing 340. The bearing 340 is somewhat different than bearing 40 of the joint prosthesis 10 of FIGS. 1 through 4.

Similar to joint prosthesis 10 of FIGS. 1 through 4, joint prosthesis 310 may further include a head 350, which is secured to the stem component 332. The head 350 cooperates with the acetabulum 26 may be connected to the head 350 by the use of a cup 342 positioned on the acetabulum 26. A liner 344 similar to liner 44 of the joint prosthesis 10 may be positioned between the cup 342 and the head 350.

While the joint prosthesis 310 may include a solitary bearing 340, as shown in FIG. 9, the joint prosthesis 310 may include a second bearing 364 similar to the first bearing 340 and positioned from the first bearing 340. As with the joint prosthesis FIGS. 1 through 4, the joint prosthesis 310 includes a body portion 356 similar to body portion 56 of the joint prosthesis 10, which body portion 356, is in intimate contact with the inner wall 330 of the long bone 312.

By providing the body portion 356 in contact with the femur, the joint prosthesis 310 provides for proximal loading, which optimizes fixation and promotes repair of the cortical bone. The first bearing 340 and the second bearing 364 serve to provide the distal portion 334 of the stem component 332 in a space-apart relationship from the inner wall 330 of the long bone 312.

Figure 10:
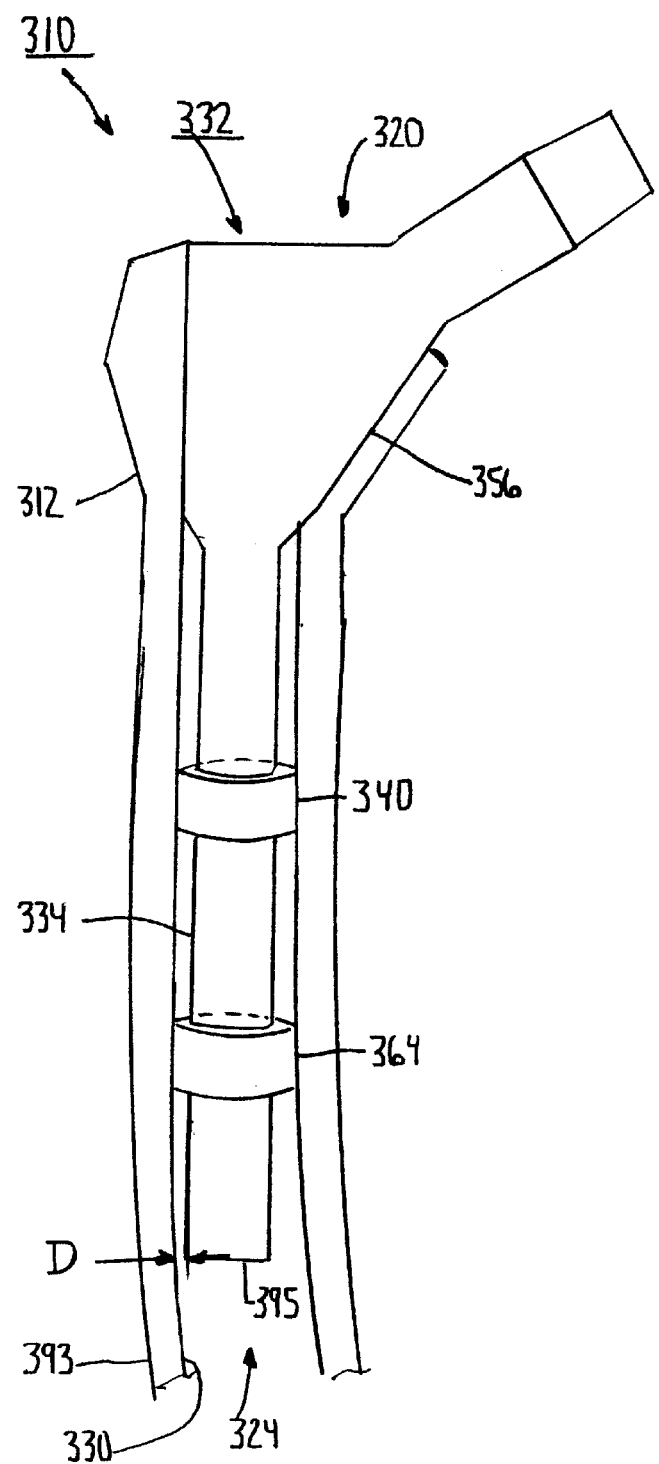
FIG. 10 is a partial perspective view partially in cross section of the hip stem and bearings of FIG. 9 showing the stem and bearings in a femur having an arcuate shape.

Referring now to FIG. 10, the joint prosthesis 310 is shown implanted in long bone 312 having a curved portion 393 into which the distal portion 334 of the femoral component 332 extends. Since the distal portion 334 of the femoral component 332 of the joint prosthesis 310 is smaller than the canal 324, the femoral component 332 can accommodate a long bone 312 which has a portion of the long bone 312 which is curved such as curved portion 393.

The use of the femoral component 332 with the smaller distal portion 334 eliminates the need for a femoral component 332 which is specifically designed to accommodate the particular curved portion which may exist in the distal portion of long bones. Therefore, when utilizing the joint prosthesis 310, the distal portion 334 may extend quite distally, even into the curved portion 393 of the long bone, to provide additional support to the prosthesis.

As shown in FIG. 10, the distal end 395 of the distal portion 334 of the femoral component 332 may still be spaced a distance D from the inner wall 330 of the long bone 312. Thus, even when inserted in the curved portion 393 of the long bone 312, the stem component 332 is not in contact with or causing thigh pain to the long bone 312.

Figure 11:
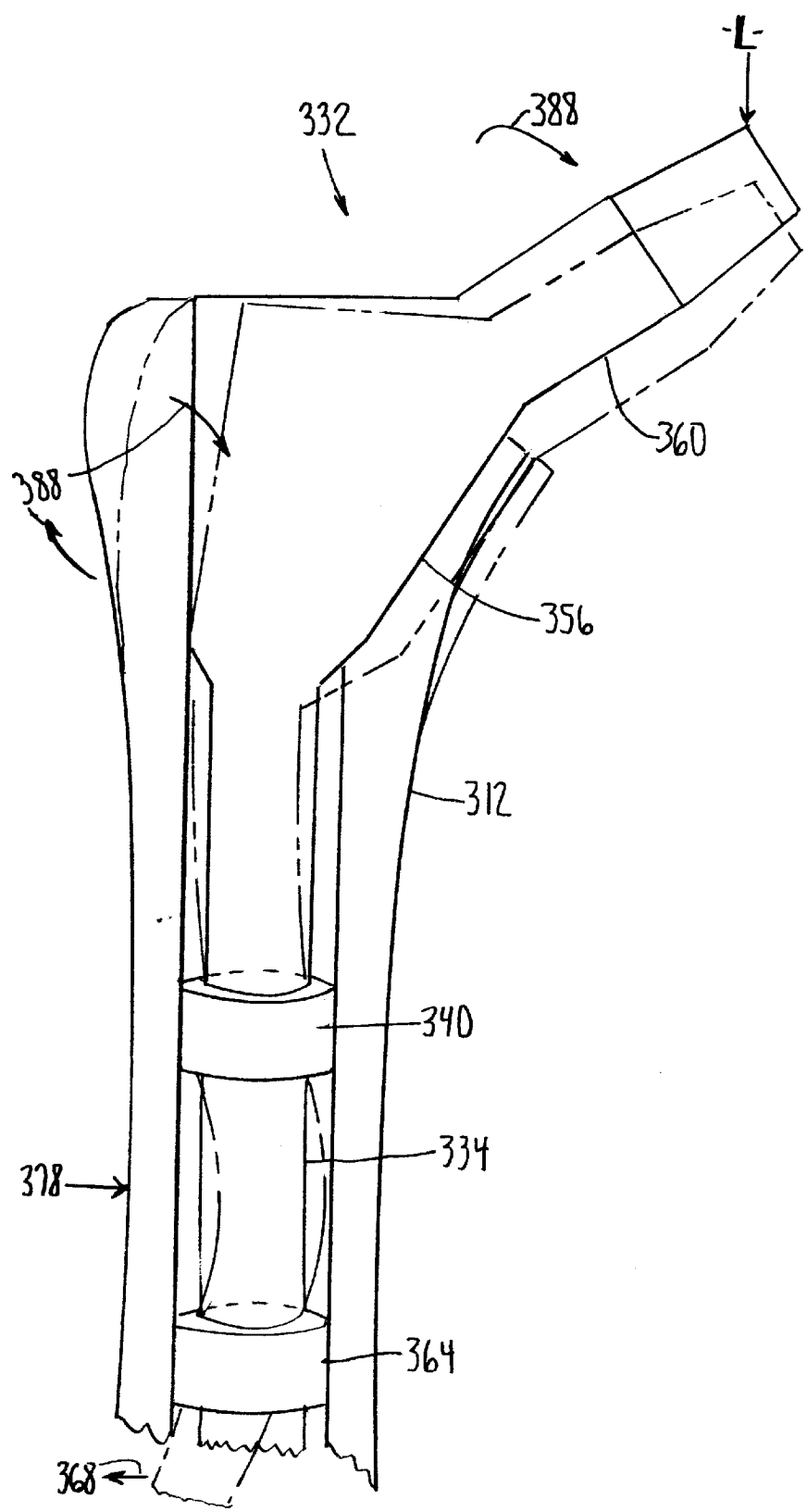
FIG. 11 is a partial perspective view partially in cross section of the hip stem of FIG. 9 showing the stem and bearings under load.

Referring now to FIG. 11, the joint prosthesis 310 is shown in position in the long bone 312 with a load -L- applied to neck 360 of the femoral component 332. As shown in FIG. 11, the distal portion 334 is restrained by first bearing 340 and second bearing 364. As the body portion 356 of the stem component 332 rotates in the direction of arrows 388, the distal portion 334 of the femoral component 332 is permitted to bend in the direction of arrow 378 between the first bearing 340 and the second bearing 364 and in the direction of arrow 368 in a position distal to the second bearing 364. Thus, the joint prosthesis 310 provides for a deflected stem component 332 which may support heavy loads without large concentrated stresses.

Figure 12:
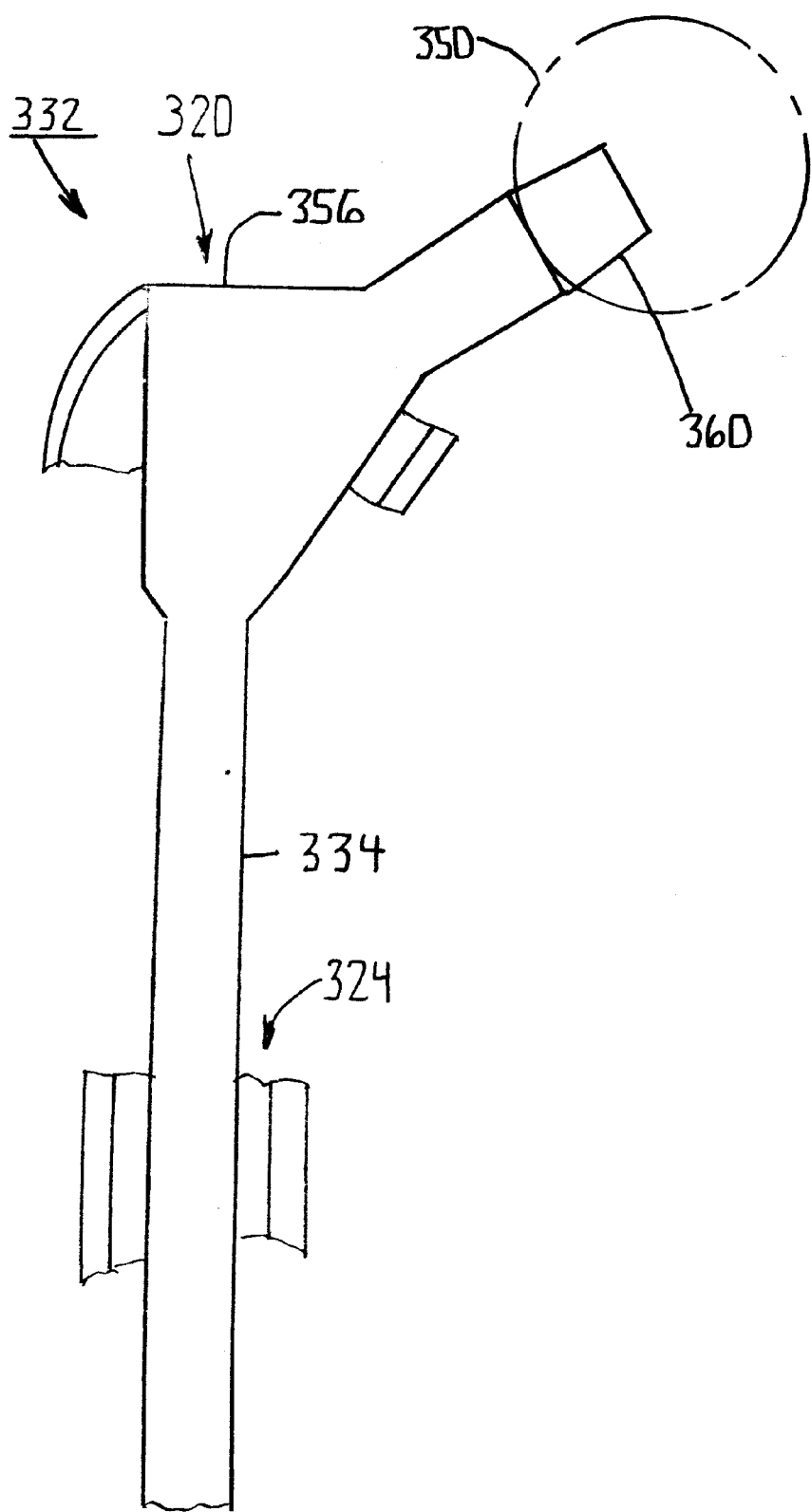
FIG. 12 is a partial perspective view partially in cross section of the hip stem of FIG. 9 showing the curved distal portion of the stem and bearings in greater detail.
Figure 13:
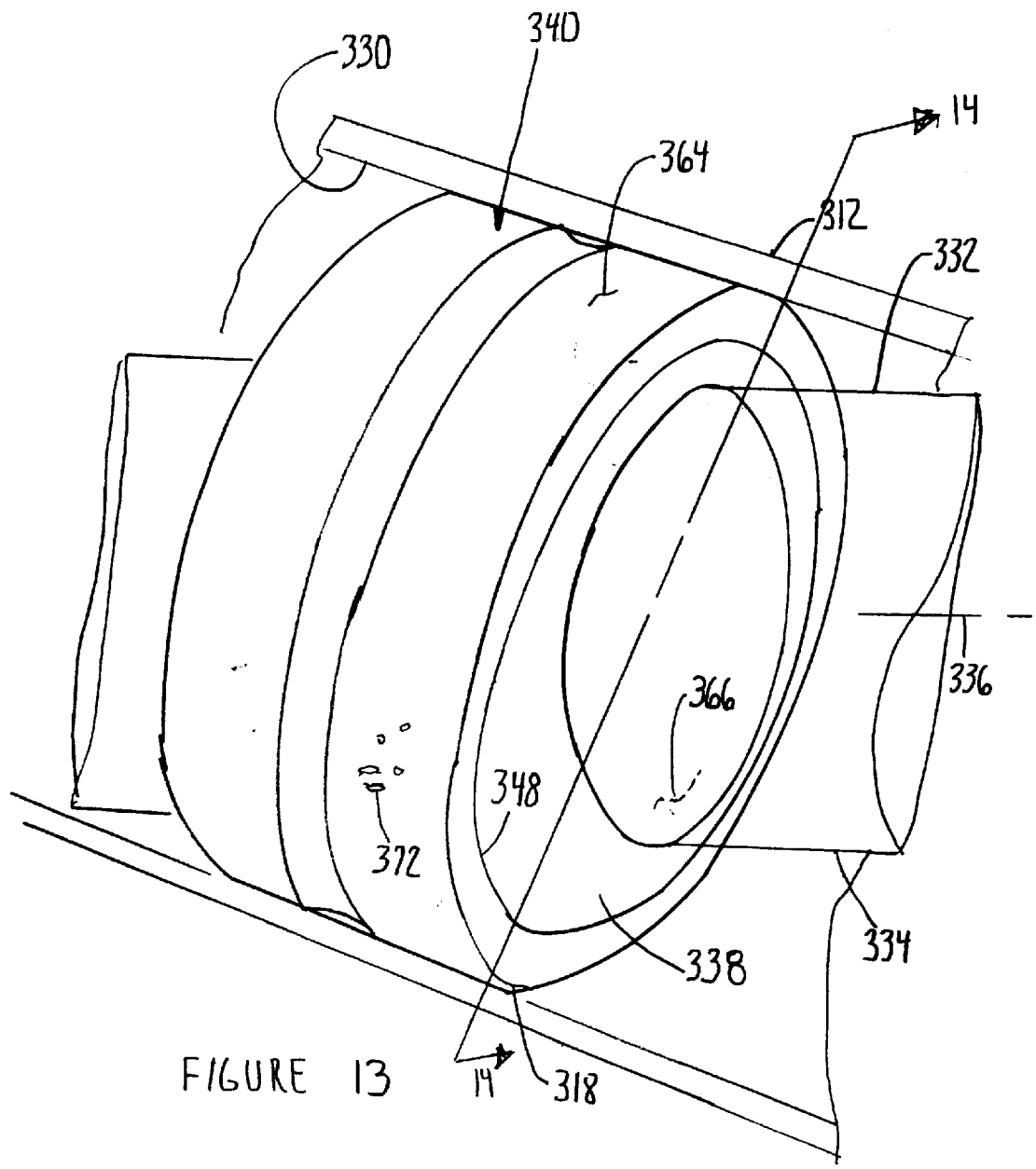
FIG. 13 is an enlarged plan view of the hip stem of FIG. 9 showing the stem in greater detail.

Referring now to FIG. 12, the femoral component 332 is shown in greater detail. The stem component 332 as shown in FIG. 13 includes a body portion 356. Extending from the body portion 356 approximately is neck portion 360. Extending distally from body portion 356 is the distal portion 334. The body portion 356 may be shaped to conform to the cavity 320 formed in the proximal resected portion of a long bone. The distal portion 334 is preferably shaped to conform to the canal 324 and is generally cylindrical. The neck portion 360 provides support between body 356 and the head 350.

Referring now to FIG. 13, the bearing 340 is shown in greater detail. As shown in FIG. 13, the bearing 340 is adapted for permitting angular movement of the stem component 332 with respect the long bone 312 along the longitudinal axis 336 of the stem component 332.

Figure 14:
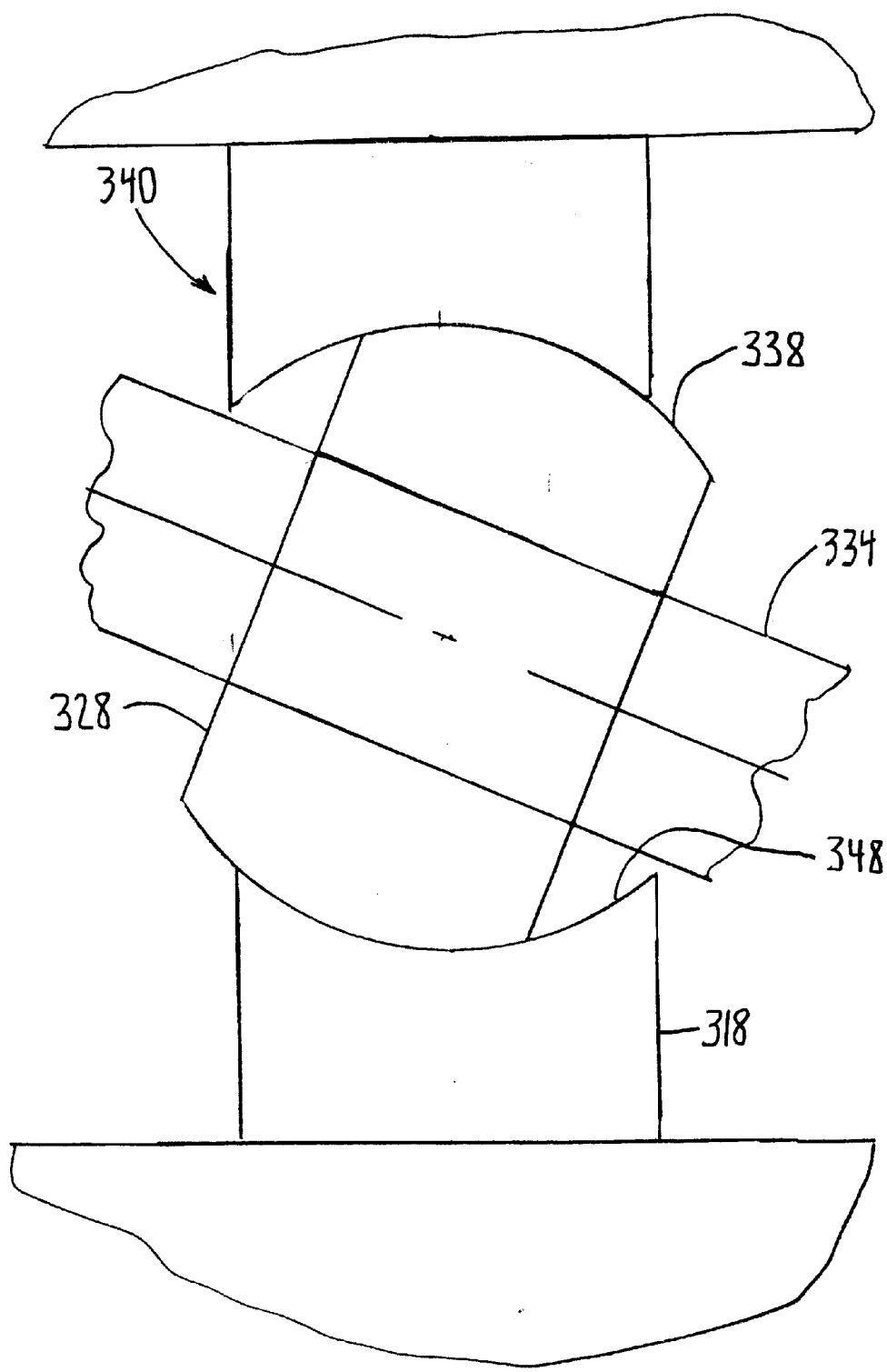
FIG. 14 is a partial perspective view partially in cross section of the bearings of FIG. 9 showing the bearings in greater detail.

Referring to FIGS. 13 and 14, the bearing 340 includes an outer ring 318 and an inner ring 328. As shown in FIGS. 13 and 14, the inner ring 328 is angularly moveable with respect to the outer ring 318 along the longitudinal axis 336 of the stem component 332. The angular movement between the outer ring 318 and inner ring 328 may be accommodated in many ways. For example, the inner ring and outer ring may be interconnected by a bonded flexible material or be otherwise mechanically interlocked.

Alternatively, as is shown in FIGS. 13 and 14, the inner ring 328 may include a spherical outer periphery 338 which mates with a spherical inner periphery 348 on the outer ring 318. As with the bearing 40 of bearings FIGS. 1 through 4, the bearing 340 may include a feature 372 in the form of, for example, Porocoat®, to provide for bone ingrowth between the periphery 330 of the long bone 312 and outer surface 364 of the outer ring 318 of the bearing 340.

Figure 15:
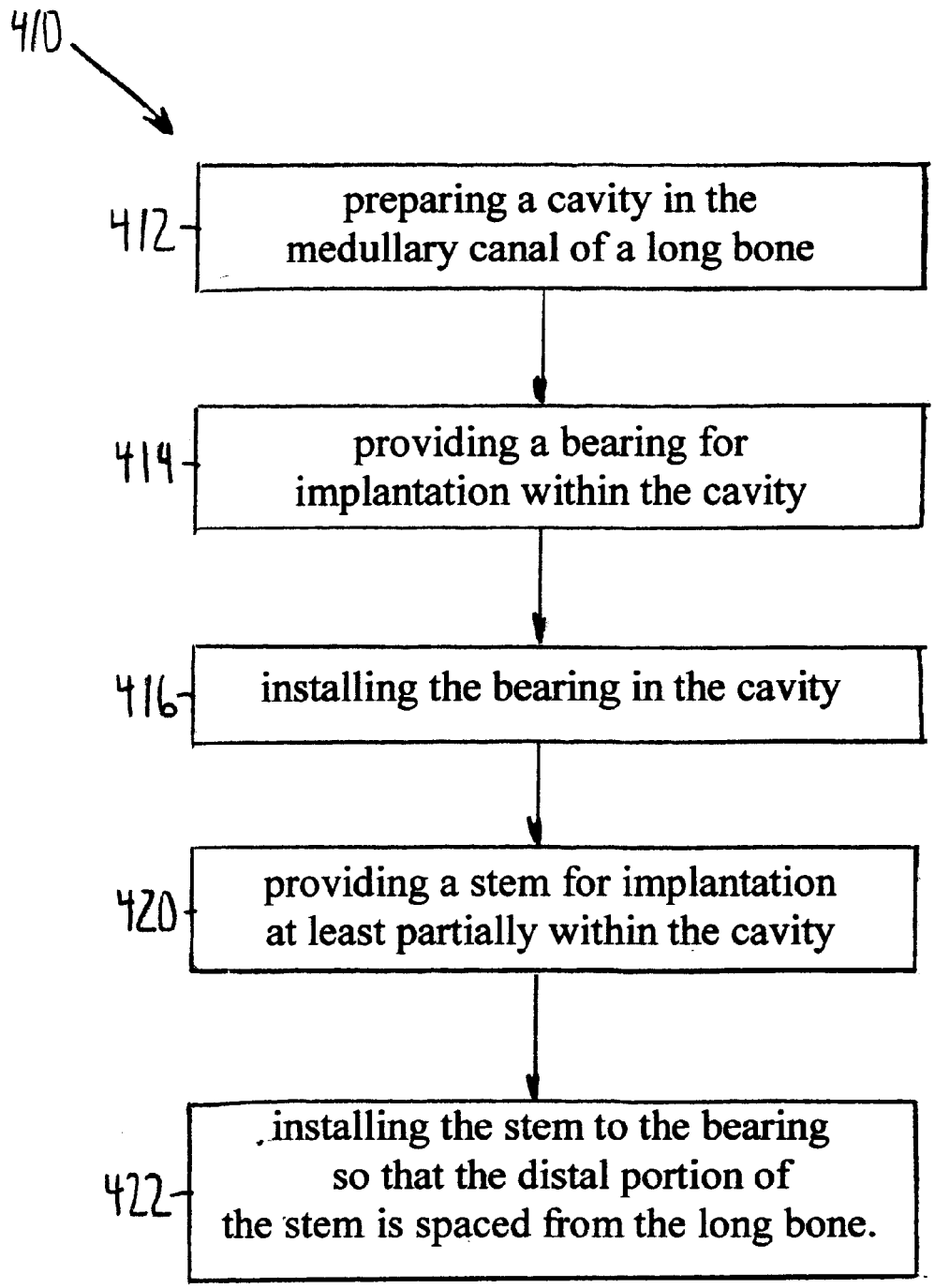
FIG. 15 is a process flow chart for a method of providing total hip arthroplasty according to the present invention.

Referring now to FIG. 15, a method 410 for performing joint arthoplasty is shown. The method 310 a first step 412 of preparing a cavity in the medullary canal of a long bone. The method also includes a second step 414 of providing a bearing for implantation within the cavity. The method also includes a third step 416 of installing the bearing in the cavity.

The method 410 for performing joint arthroplasty also includes a fourth step 420 of providing a stem for implantation at least partially within the cavity. The method further includes a fifth step 422 of installing the stem to the bone so that the distal portion of the stem is spaced from the long bone.

The method 410 of performing joint arthroplasty may include a method where the second step of providing the cavity for implantation within the cavity includes the step of providing two bearings and where the step of installing the bearing in the cavity comprises installing two bearings into the cavity.

The method 410 of performing joint arthroplasty may be modified such that the step of installing the bearing includes collapsing the bearing and inserting the bearing in the collapsed condition into the cavity and then permitting the bearing to expand.

The method 410 of performing joint arthroplasty may also include a step of honing the bone canal to provide a location to install the bearing.

Figure 16:
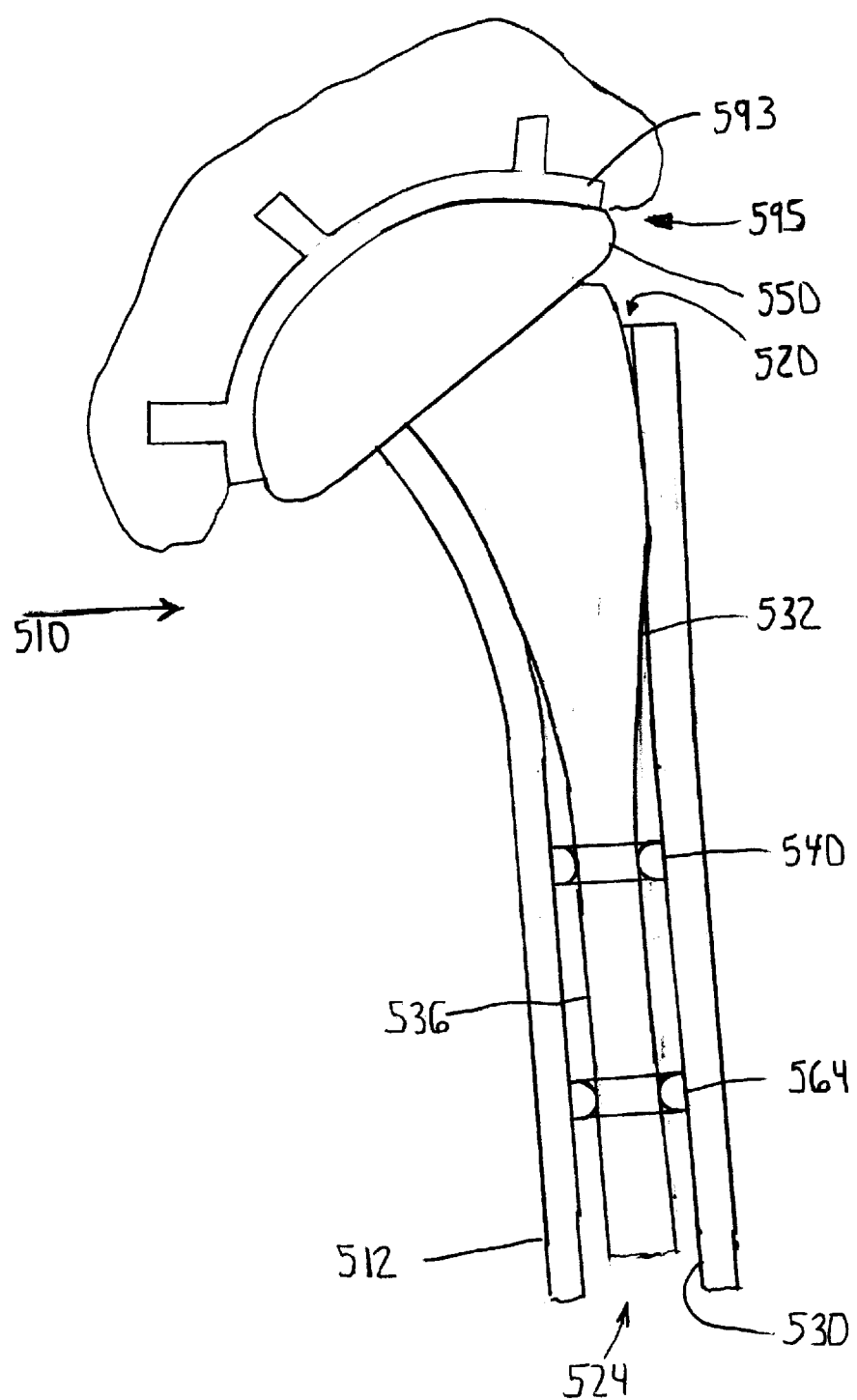
FIG. 16 is a partial perspective view partially in cross section of a shoulder prosthesis including a stem, bearings and ball for implanting into a humerus and glenoid in accordance with another embodiment of the present invention.

Referring now to FIG. 16, an alternate embodiment of the present invention is shown as joint prosthesis for 510. The joint prosthesis for 510 is similar to prosthesis 10 except that the joint prosthesis 510 is for utilization in a shoulder joint while joint prosthesis 10 is for use in a hip joint.

The joint prosthesis for 510 includes a stem component 532 similar to component 32 of the prosthesis 10. The joint prosthesis for 510 further includes a first bearing 540, which is similar to the bearing 40 of FIGS. 1 through 4. It should be appreciated, however, that the first bearing 540 may be similar to the first bearing 340 of FIGS. 9 through 12. The joint prosthesis 510 may also include a head 550, which extends from stern component 532. The joint prosthesis 510 may further include a glenoid component for 593, which is fitted onto glenoid cavity 595. The first bearing 540 is fitted into opening 520 and rests in cavity 524 against inner wall 530 of long bone 512. The first bearing 540 includes a central opening into which distal portion 536 of the stem component 532 fits. It should be appreciated that similar to the joint prosthesis 10; the joint prosthesis 510 may include a second bearing 564 which is similar to in space from the first bearing 540.

The bearing 40 may be made of any suitable durable material and may for example be made of a plastic or a metal. If the bearing is made of a plastic or metal, it should be sterilizable and compatible with the human autonomy. If made of a metal, the bearing 40 may be made of, for example, colbot chrome alloy steel, stainless steel, or a titanium alloy. It should be appreciated that the bearing 40 may likewise be made of a ceramic material.

By providing a joint prostheses with a bearing which supports the distal stem of the prostheses in a spaced-apart relationship from the bone canal, a prostheses can be provided which keeps the proximal portion of the prosthetic stem from being subjected to forces that could dislodge the device. The prosthesis allows the transmission of forces in the long bone in a manner that simulates the natural transmission of load and improves the physiological loading of the bone. Stress shielding is thus reduced, leading to the retention of natural bone.

By providing a prosthesis, which includes a bearing which spaces the distal stem from the inner wall of the long bone, stems can be easily made flexible because the diameter of the stem can take any size as long as it is smaller than the bone canal. The bone can thus receive natural stresses and prevent the exterior of the stem from rubbing against the canal of the long bone. The elimination of the rubbing of the tip of the stem reduces thigh pain when used in hips. Further, the prevention of the rubbing of the stem against the canal will reduce the probability that a stem will fracture the femur when exposed to trauma.

Because the stem is flexible, the seating of the proximal portion of the device is not dictated by the stem (because the stem is flexible and does not contact the bone canal directly). This allows superior seating of the proximal portion of the device and superior bone ingrowth in the proximal area. This may reduce osteolysis from wear debris.

By providing a prosthetic joint, including a bearing that has a limited axial length of contact, the amount of bone that must be reamed is limited to the length of contact of the bearing. The amount of bone that must be reamed from the bone canal is thereby reduced. The reduction of the amount of bone that must be removed will reduce patient pain and increase patient comfort.

By providing a prosthetic joint, including a stem which has a bearing, straight stems may be inserted past the curved portion of the long bone without being bent or causing interference with the curved portion of the long bone.

By utilizing the bearing of the present invention in an intramedullary rod, an intramedullary rod can be provided which has rods that fill only the canal defect area. The rods could be spaced from the non-defect portion of the bone. The smaller distal ends of the rod would be spaced from the bone such that the rods may no longer need to be removed from the bone. The removal is not required because the transmission of stress in the healed bone will duplicate natural bone stress transmission more naturally.

Although the present invention and its advantages have been described in detail, it should be understood that various changes, substitutions, and alterations can be made therein without departing from the spirit and scope of the present invention as defined by the appended claims.

I claim:

1. A joint prosthesis for cooperation with a long bone and a second bone for use in arthroplasty, a cavity being formed in the long bone and defined by an inner wall of the long bone, the prosthesis comprising:
    a stem component including a distal portion thereof for placement at least partially within the cavity of the long bone and for securing thereto, said stem component defining a longitudinal axis thereof; and
    a bearing for placement in the cavity between said stem component and the long bone so that the distal portion of said stem component is spaced from the inner wall of the long bone, wherein said bearing is adapted for permitting angular movement of said stem component with respect to the long bone along the longitudinal axis of said stem component.

2. The joint prosthesis of claim 1, further comprising a second bearing spaced from said first mentioned bearing.

3. The joint prosthesis of claim 1, wherein said bearing comprises a outer ring for cooperation with the bone and an inner ring for cooperation with said stem component, the inner ring being angularly movable with respect to the outer ring along the longitudinal axis of said stem component.

4. The joint prosthesis of claim 3:
    wherein the inner ring defines a spherical outer periphery thereof; and
    wherein the outer ring defines a spherical inner periphery thereof, the outer periphery and the inner periphery defining pivoting motion therebetween.

5. The joint prosthesis of claim 1:
    wherein the distal portion of said stem component is generally cylindrical and defines a stem diameter thereof; and
    wherein the distal portion of the cavity is generally cylindrical and defines a cavity diameter thereof, the stem diameter being less than 70 percent of the cavity diameter.

6. A hip joint prosthesis for cooperation with a femur for use in arthroplasty, a cavity being formed in the femur and defined by an inner wall of the femur, the prosthesis comprising:
    a femoral component including a portion thereof for placement at least partially within the cavity of the femur, said femoral component defining a longitudinal axis thereof;
    a cup for attachment to the acetabulum and for cooperation with said femoral component; and
    a bearing for placement in the cavity between said femoral component and the femur so that the distal portion of said femoral component is spaced from the inner wall of the femur, wherein said bearing is adapted for permitting angular movement of said femoral component with respect to the femur along the longitudinal axis of said femoral component.

7. The hip joint prosthesis of claim 6, further comprising a second bearing spaced from said first mentioned bearing.

8. The hip joint prosthesis of claim 6, wherein said bearing comprises:
    an outer ring for cooperation with the femur; and
    an inner ring for cooperation with the femoral component, said inner ring being angularly movable with respect to said outer ring along the longitudinal axis of said femoral component.

9. The hip joint prosthesis of claim 8:
    wherein said inner ring defines a spherical outer periphery thereof; and
    wherein said outer ring defines a spherical inner periphery thereof.

10. The hip joint prosthesis of claim 6:
    wherein the distal portion of said stem is generally cylindrical and defines a stem diameter thereof; and
    wherein the distal portion of the cavity is generally cylindrical and defines a cavity diameter thereof, the stem diameter being less than 70 percent of the cavity diameter.

11. A joint prosthesis for cooperation with a long bone and a second bone for use in arthroplasty, a cavity being formed in the long bone and defined by an inner all of the long bone, the prosthesis comprising:
    a stem component including a distal portion thereof for placement at least partially within the cavity of the long bone and for securing thereto, said stem component defining a longitudinal axis thereof; and a bearing for placement in the cavity between said stem component and the long bone so that the distal portion of said stem component is spaced from the inner wall of the long bone, wherein said bearing comprises a split ring.

12. A joint prosthesis for cooperation with a long bone and a second bone for use in arthroplasty, a cavity being formed in the long bone and defined by an inner wall of the long bone, the prosthesis comprising:

a stem component including a distal portion thereof for placement at least partially within the cavity of the long bone and for securing thereto, said stem component defining a longitudinal axis thereof; and a bearing for placement in the cavity between said stem component and the long bone so that the distal portion of said stem component is spaced from the inner wall of the long bone, wherein said bearing comprises a ring having a cylindrical outer periphery and a convex inner periphery.

13. A joint prosthesis for cooperation with a femur for use in arthroplasty, a cavity being formed in the femur and defined by an inner wall of the femur, the prosthesis comprising:

a femoral component including a portion thereof for placement at least partially within the cavity of the femur, said femoral component defining a longitudinal axis thereof;

a cup for attachment to the acetabulum and for cooperation with said femoral component; and a bearing for placement in the cavity between said femoral component and the femur so that the distal portion of said femoral component is spaced from the inner wall of the femur, wherein said bearing comprises a split ring.

14. A joint prosthesis for cooperation with a femur for use in arthroplasty, a cavity being formed in the femur and defined by an inner wall of the femur, the prosthesis comprising:

a femoral component including a portion thereof for placement at least partially within the cavity of the femur, said femoral component defining a longitudinal axis thereof;

a cup for attachment to the acetabulum and for cooperation with said femoral component; and a bearing for placement in the cavity between said femoral component and the femur so that the distal portion of said femoral component is spaced from the inner wall of the femur, wherein said bearing comprises a ring having a cylindrical outer periphery and a convex inner periphery.

15. A bearing for use in a joint prosthesis for use in arthroplasty, the bearing being adapted for cooperation with a stem component placed at least partially in a cavity formed in a long bone and defined by an inner wall of the long bone, the bearing being adapted for placement in the cavity between the stem component and the long bone so that the distal portion of the stem component is spaced from the inner wall of the long bone, wherein said bearing is adapted for permitting angular movement of the stem component with respect to the long bone along the longitudinal axis of the stem component.

16. A bearing for use in a joint prosthesis for use in arthroplasty, the bearing being adapted for cooperation with a stem component placed at least partially in a cavity formed in a long bone and defined by an inner wall of the long bone, the bearing being adapted for placement in the cavity between the stem component and the long bone so that the distal portion of the stem component is spaced from the inner wall of the long bone, wherein said bearing comprises a split ring.

17. A bearing for use in a joint Prosthesis for use in arthroplasty, the bearing being adapted for cooperation with a stem component placed at least partially in a cavity formed in a long bone and defined by an inner wall of the long bone, the bearing being adapted for placement in the cavity between the stem component and the long bone so that the distal portion of the stem component is spaced from the inner wall of the long bone, wherein said bearing comprises a ring having a cylindrical outer periphery and a convex inner periphery.

* * * * *